United States Patent
Rehkemper et al.

(10) Patent No.: US 6,739,782 B1
(45) Date of Patent: May 25, 2004

(54) ORAL CLEANING DEVICE WITH INTERNAL WATER BLADDER

(75) Inventors: Steven Rehkemper, Chicago, IL (US); Peter Greenley, Chicago, IL (US)

(73) Assignee: Rehco, L.L.C., Chicago, IL (US)

( * ) Notice: Subject to any disclaimer, the term of this patent is extended or adjusted under 35 U.S.C. 154(b) by 0 days.

(21) Appl. No.: 10/388,539

(22) Filed: Mar. 17, 2003

(51) Int. Cl.[7] .......................... A46B 11/04; B43K 5/04; A61C 17/00
(52) U.S. Cl. .......................... 401/279; 401/278; 401/152; 401/156; 433/89; 433/80
(58) Field of Search .................... 401/279, 278, 401/270, 145, 152, 153, 156, 187, 190; 433/80, 82, 89, 141; 222/79, 92, 105, 107, 206, 213, 215; 72/89, 90, 91, 72

(56) References Cited

U.S. PATENT DOCUMENTS

| | | | | |
|---|---|---|---|---|
| 2,506,035 A | * | 5/1950 | Parker | 401/143 |
| 3,486,539 A | * | 12/1969 | Jacuzzi | 141/329 |
| 4,257,460 A | * | 3/1981 | Paranay et al. | 141/26 |
| 4,735,239 A | * | 4/1988 | Salmon et al. | 141/25 |
| 6,193,107 B1 | * | 2/2001 | D'Andrade | 222/79 |

* cited by examiner

Primary Examiner—David J. Walczak

(57) ABSTRACT

A handheld portable oral cleaning device that includes a refillable internal bladder, which a user is able to fill with a liquid. The bladder is preferably an expandable but resilient latex rubber. One end of the bladder is accessible to the user, such that the user may fill the bladder with a liquid, such as water from a faucet. As the bladder fills with water it expands and exerts a pressure on the water as the bladder has a tendency to return to its original unfilled form. The pressurized water may then be sprayed out of the oral cleaning device to assist in cleaning the user's mouth.

12 Claims, 4 Drawing Sheets

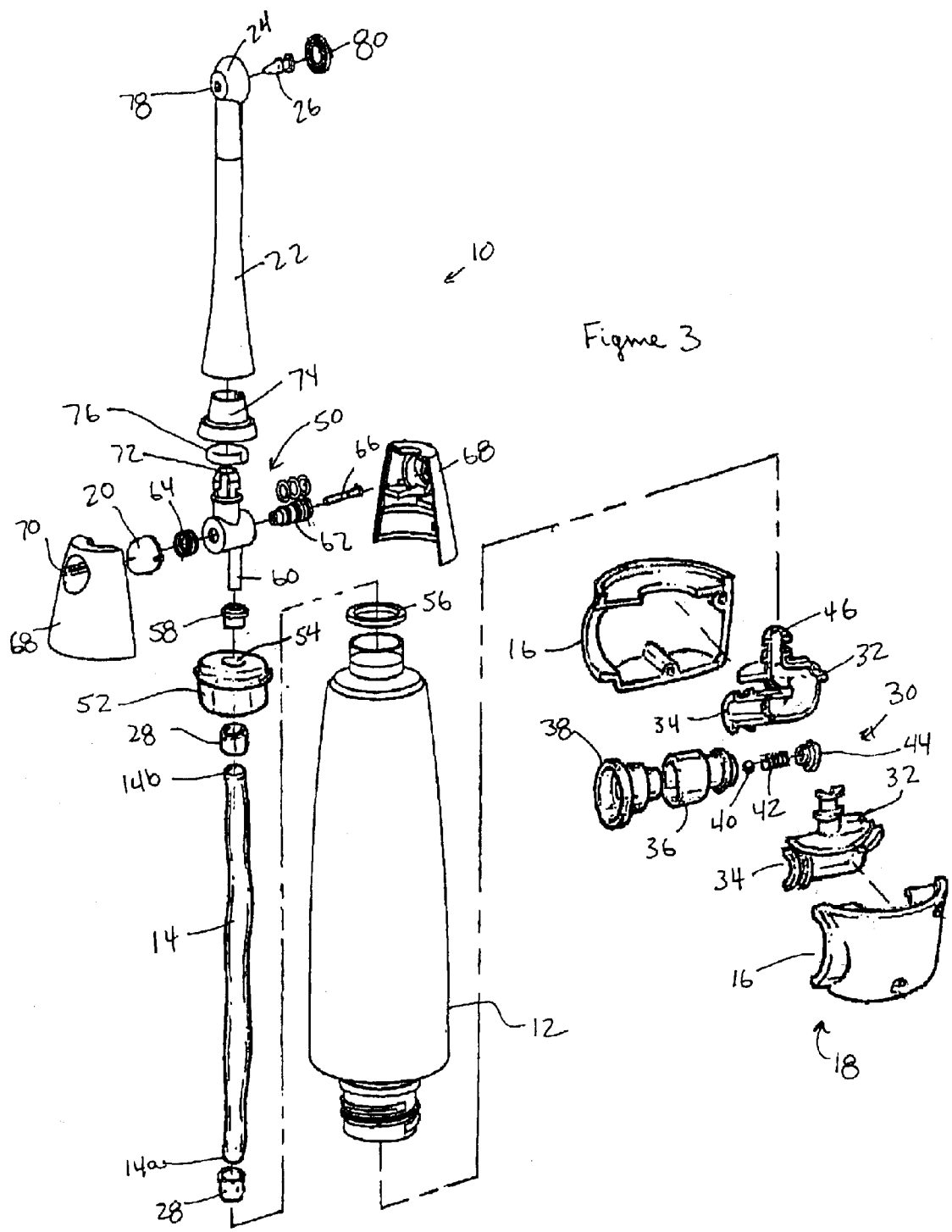

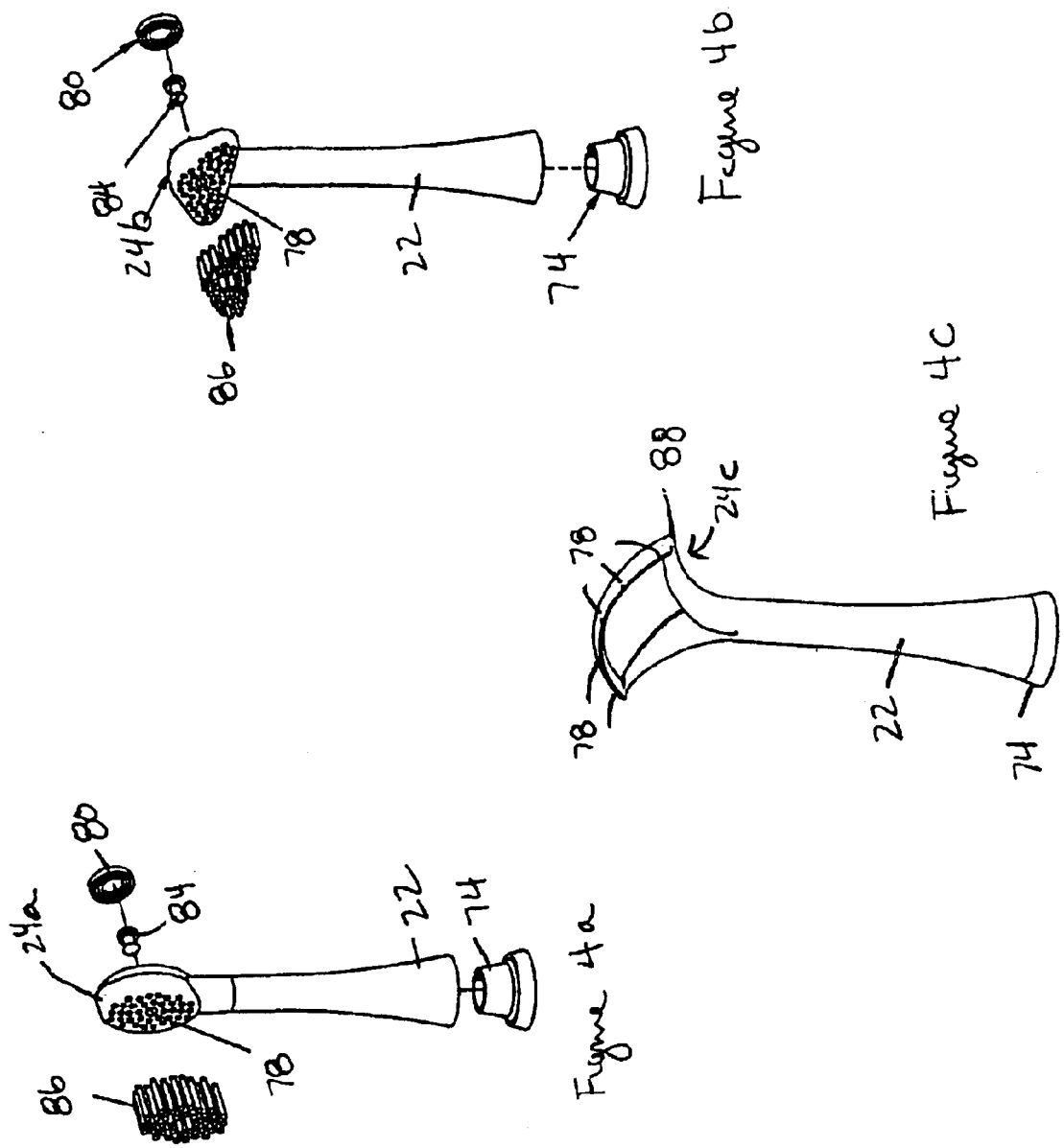

ORAL CLEANING DEVICE WITH INTERNAL WATER BLADDER

FIELD OF THE INVENTION

The present invention relates to oral cleaning devices such as toothbrushes and water jets and in particular to an oral cleaning device with an internal water bladder.

BACKGROUND OF THE INVENTION

Oral cleaning devices that employ a water jet feature are known in the art and typically use an external supply of water. In one category of the prior art, a toothbrush is tethered or connected to a faucet. The water pressure from the faucet is used to propel the water out the head of the toothbrush and/or used to power a motor that is used to rotate or move bristles. For example, U.S. Pat. No. 5,304,010 discloses a toothbrush that includes a hollow body, an opening by the head of the toothbrush, and a water inlet that is tethered and attached to a faucet. In another example, U.S. Pat. No. 4,181,997 discloses a toothbrush that is also tethered to a faucet and that uses the water pressure to power an impeller to move bristles on the head of the toothbrush. In both patents, the water is already pressurized and flowing. Additional toothbrushes that are tethered to a faucet or external source of running water may be found in U.S. Pat. No. 5,863,192, discloses a toothbrush tethered to a shower head; U.S. Pat. Nos. 5,500,973 and 4,257,433, disclose toothbrushes tethered to faucets; and U.S. Pat. No. 4,412,823, discloses a toothbrush tethered to an external source of water that is pumped into and through the toothbrush.

Various problems exist and are associated with the fact that the toothbrush must be tethered to the external source at all times. These toothbrushes significantly limit the user's range of motion. In addition, the units are bulky and are not made to be portable, oftentimes causing the user to own a separate toothbrush for traveling.

Other devices that are non-tethered require batteries or some other type of power supply to propel the fluid out of the device. If the device is plugged into an electrical socket it is still tethered to a device. Moreover, these devices may become unsafe as the liquid may spray or splash near the electrical socket. For the devices that use batteries, the money associated with replacement batteries increase the cost of the device making it undesirable to consumers.

As such it is an object of the present invention to provide a totally non-tethered portable oral cleaning device. It is also an object of the present invention to provide an oral cleaning device that incorporates a nozzle for jetting a pressurized fluid into a user's mouth. The oral cleaning device should be capable of operating without the use of batteries or additional power supplies. The oral cleaning device in accordance with the present invention includes a resilient internal expandable bladder for holding a liquid. The bladder is contained within the oral cleaning device eliminating the need to tether the device to a faucet or other outside source. The oral cleaning device also includes a means for releasing the liquid contained within the bladder out of the oral cleaning device, without the need of batteries or pumps. The oral cleaning device is completely portable and assists the user in cleaning their entire mouth, including the tongue, gums, and teeth, by providing interchangeable heads. The user is required only to fill the internal bladder with a liquid. Once filled, the expandable bladder exerts a substantially constant force on the liquid, as the bladder desires to return to its original form. Thus, when the liquid contained in the bladder is released, the pressure exerted on the liquid, by the bladder, propels the liquid out of the device.

SUMMARY OF THE INVENTION

In accordance with the present invention, a handheld portable oral cleaning device is provided that includes a refillable internal bladder, which a user is able to fill with a liquid. The bladder is an expandable but resilient latex rubber. One end of the bladder is accessible to the user, such that the user may fill the bladder with a liquid, such as water from a faucet. As the bladder fills with water it expands and exerts a pressure on the water because the bladder has a tendency to return to its original unfilled form. This pressure causes the water to expel or jet out of the oral cleaning device and thus assists in cleaning the user's mouth.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein:

FIG. 3 is an exploded view of the oral cleaning device of FIG. 1;

FIG. 4a is an exploded view of a head assembly that has a short nozzle and bristles to brush teeth;

FIG. 4b is an exploded view of a head assembly illustrating a tongue brush; and

FIG. 4c is an perspective view of a head assembly illustrating a tongue scraper.

DETAILED DESCRIPTION OF THE EMBODIMENTS

Figure 1:
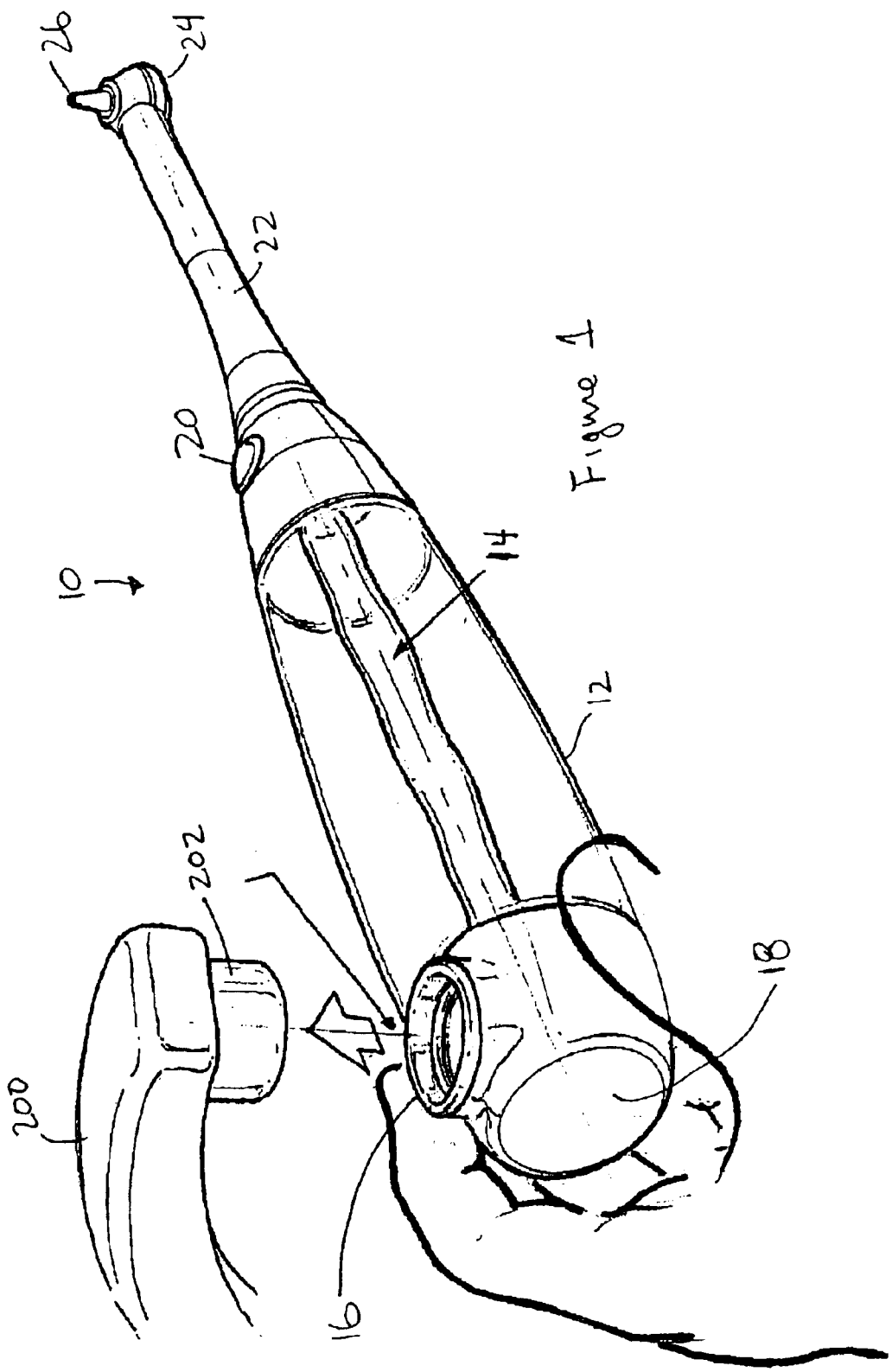
FIG. 1 is a perspective view of an oral cleaning device having a refillable expandable but resilient internal bladder, the device is being moved towards a faucet such that the bladder may be filled with water; the device is further illustrated with an empty bladder.

While the invention is susceptible to embodiments in many different forms there are shown in the drawings and will be described herein the preferred embodiments of the present invention. It should be understood, however, that the present disclosure is to be considered an exemplification of the principles of the invention and is not intended to limit the spirit or scope of the invention and/or claims by the embodiments illustrated.

Figure 2:
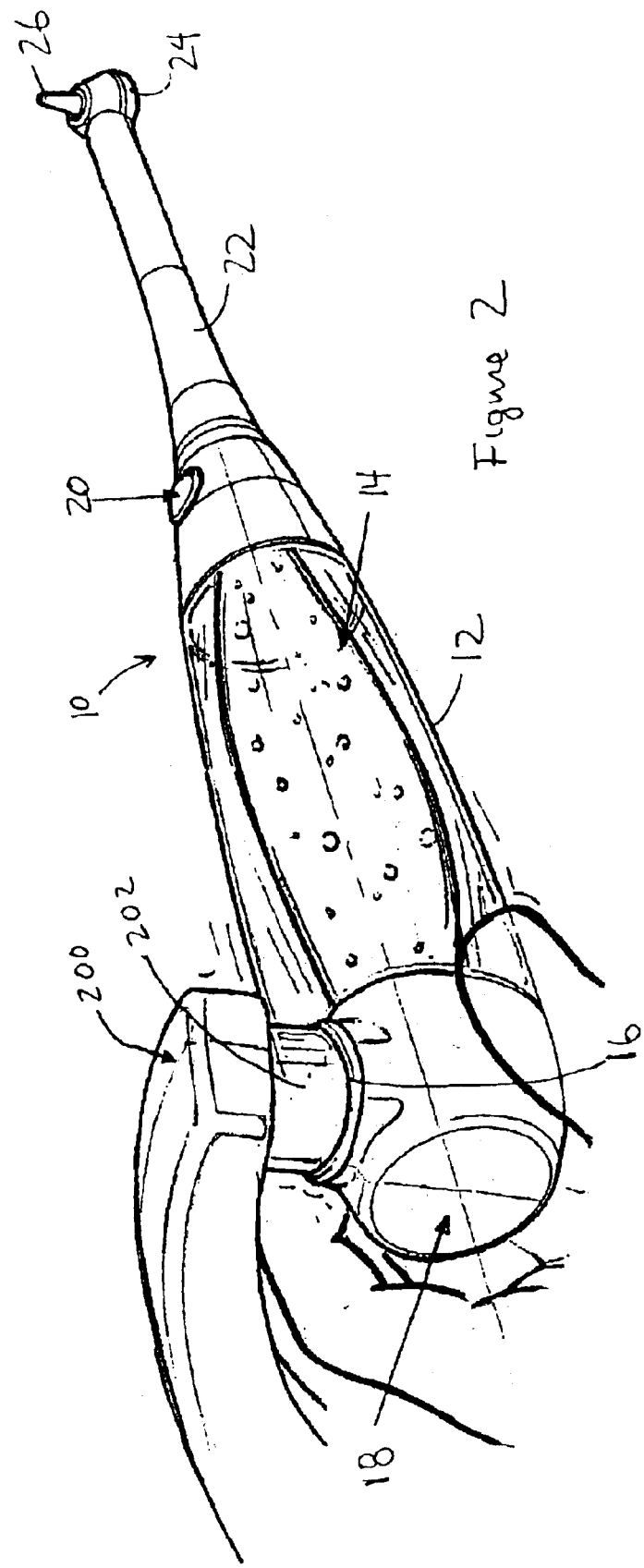
FIG. 2 is a perspective view of the oral cleaning device from FIG. 1 shown being held up to the faucet and in the process of being filled with water; the device is further illustrated with the bladder expanding as it is being filled with water.

Referring now to FIGS. 1–3, there is disclosed in accordance with the present invention an oral cleaning device generally referenced to as numeral 10. The oral cleaning device includes a body 12 (or handle) that may be gripped by a user during use. As will be described in detail below, the body 12 includes a refillable internal bladder 14 that a user may fill with a liquid, such as water from a faucet 200. The oral cleaning device 10 also includes an aperture 16, preferably positioned towards the bottom portion 18 of the device 10, but may in practice be located anywhere on the device. The aperture 16 is sized to fit around a typical faucet nozzle 202 (as shown in FIG. 2). After the aperture 16 is positioned around the faucet nozzle 202, the user may turn the faucet 200 on, permitting the water to fill and expand the bladder 14. Upon filling the bladder 14 with water, the water may be released by depressing a button 20, which opens a valve mechanism (shown in FIG. 3) that permits the water to expel out of the bladder 14. The water once released travels through a neck 22 that extends outwardly from the body 12 to a head 24, and out the head 24 via a nozzle 26 or opening. This neck/head assembly may be interchangeable with other neck/head assemblies to provide the user with different cleaning implements. Alternatively, the neck/head assembly may also be fixed onto the body 12, to provide a single cleaning implement.

The bladder 14 is positioned in the body 12 and is preferably a latex rubber but is more importantly an expandable but yet resilient material. Thus while the bladder 14 expands as it is filing with water, the resiliency of the material tends to return the bladder 14 to a normal unfilled position. This resiliency of the material exerts a pressure on the water such that the water ejects out of the bladder 14 when released. The bladder 14 is secured at one end 14a to a one-way valve inlet assembly 30 via a collar 28, which is captured in the bottom portion 18 of the device. The other end 14b of the bladder 14 is secured to a valve mechanism 50 via a collar 28.

In one embodiment of the invention, the one-way valve inlet assembly 30 includes a one-way valve 36 (40, 42, 44) that is captured within a two-piece valve housing 32. The one-way valve assembly 30 includes an inlet 34 that communicates with the aperture 16. A rubber insert 38 is captured in the aperture 16 and permits the inlet 34 to communicate effectively with a faucet nozzle 202 as well as ensure that the water entering the device does not leak throughout the bottom portion 18 or body 12 of the device 10. The rubber insert 38 can be stretched around the faucet nozzle 202 to provide a tight secure fit around a faucet nozzle. As water from the faucet passes through the aperture 16, the water pushes a ball 40 against a compression spring 42 which permits the water to enter through a valve cap 44 and then exit the valve inlet assembly 30 via an opening 46. The opening 46 is secured to the bladder 14, thus water traveling through the opening 46 will fill the bladder 14. In addition, water in the bladder 14 cannot exit the device 10 via the aperture 16 because the one-way valve inlet assembly 30 is designed to only allow water to enter the bladder 14. The bottom portion 18 may be a two-piece construction that secures the one-way valve inlet assembly 30 in place when assembled as well as attaches the bottom portion 18 to the body 12.

As mentioned above, the bladder 14 is also secured to the valve mechanism 50. This may be accomplished by placing the collar 28 that is secured to the end 14b of the bladder 14 and placing the collar 28 in communication to an opening 54 in a cap 52. The cap 52 and a cap gasket 56 is secured to the body 12. The opening 54 is reinforced with a grommet 58 that places the bladder 14 in fluid communication with an inlet 60 defined in the valve mechanism 50. The valve mechanism 50 also includes a valve piston 62 that may be moved to an open position (allowing liquid or fluid to travel through) by a button 20. A valve spring 64 exerts a force onto the button 20 and the valve piston 62 that normally keeps the valve mechanism 50 in a closed position (not allowing liquid or fluid to travel through). A valve pin 66 holds the button 20 in position with the valve piston 62 and valve spring 64. The valve mechanism 50 and other components described for opening and closing the mechanism 50 is housed within a two piece housing 68. The front portion of the housing 68 includes an opening 70 to permit the button 20 to be pressed by a user. As mentioned, the valve mechanism 50 is in a closed position unless the button 20 is pressed and held down by a user.

When the valve mechanism 50 is opened, the bladder 14 wanting to return to its normal unfilled position exerts pressure on the water forcing the water through the valve mechanism 50 and out an exit 72 defined thereon. The exit 72 of the valve mechanism 50 is in fluid communication with a channel (not shown) running through the neck 22. The neck 22 is secured to a neck base 74 that is removably attached to the exit 72. A O-ring 76 is preferably positioned between the neck base 74 and the two piece housing 68. The channel travels through the neck 22 to at least one opening 78 in the head 24. Preferably a nozzle 26 is positioned in the opening 78 and in communication with the channel, and sealed with a nozzle cap 80. The nozzle may either be a long nozzle 26 for a head 24 that acts as a water jet (more commonly used as a flossing action to clean between teeth and to clean gums. (where the teeth and gums define a first portion of a user's mouth and a second portion of the user's mouth respectively), as illustrated in FIGS. 1–3) or a short nozzle 84 for a head that also contains bristles 86 (FIGS. 4a and 4b) used to brush and rinse teeth or a head that is shaped to scrap a user's tongue (FIG. 4c) (where the tongue defines a third portion of the user's mouth). A short nozzle 84 is preferably used when brushing or scraping because the nozzle does not interfere.

In FIG. 4a, the head 24a contains bristles 86 and a short nozzle 84. In addition the head 24a is shaped to provide the user with a brush better suited for their teeth, along with a nozzle to jet liquid or fluid for cleaning gums and teeth and rinsing. In FIG. 4b, the head 24b contains a short nozzle 84 and a plurality of bristles 86 but contains a wider cross section than the head 24a in FIG. 4a. This provides the user with a cleaning device that is better suited to clean the user's tongue. In FIG. 4c, the head 24c does not contain bristles or a nozzle, the head 24c includes a projected edge 88 to scrape the user's tongue. The head 24c defined as a tongue scrape also includes at least one opening but preferably multiple openings 78 to spray liquid while the user is scrapping their tongue.

While as explained above the present invention includes the ability to jet out a liquid such as water, any type of fluid, such as a gas, may be used. For example, the user may simply pump gas into the bladder 14, as long as the pressure of the gas entering the bladder 14 is strong enough to fill bladder 14. Once the reservoir contains a sufficient amount of pressurized gas, the user may release it by pressing the button. While a gas may not be as efficient for cleaning, in some instances the liquid, may be too sensitive for the user.

With the onset of mechanical and electrical toothbrushes the total cost of the oral cleaning devices have increased. To offset the overall price of the devices the heads of the toothbrushes have been made replaceable. As such, after the bristles become worn from continual use, the head may be replaced without replacing the whole unit. However, the worn heads are simply replaced with an identical head to provide the same type of cleaning. The ability to interchange heads to provide different types of cleaning is not widely incorporated with prior art oral cleaning devices. The various interchangeable heads discussed above may be incorporated therewith to provide the user with a total cleaning experience.

From the foregoing and as mentioned above, it will be observed that numerous variations and modifications may be effected without departing from the spirit and scope of the novel concept of the invention covering a self-contained device incorporating an internal bladder positioned within the device and in fluid communication with and a nozzle into a single device. It is to be understood that no limitation with respect to the specific methods and apparatus illustrated herein is intended or inferred. It is intended to cover by the appended claims all such modifications as fall within the scope of the claims.

We claim:

1. An oral cleaning device comprising:
    a bladder contained within a body, the bladder is expandable to hold fluid and resilient to exert a pressure on fluid contained therein;
    a bottom portion attached to the body and having a one-way valve assembly attached to one end of the bladder, the one-way valve assembly in communication with an aperture defined on the bottom portion that allows fluid to enter the bladder;
    a neck and head assembly attached to the body, the neck and head assembly includes an aperture in fluid communication with another end of the bladder and is configured for expelling fluid and includes bristles for cleaning a portion of a user's mouth; and
    a mechanism disposed between the neck and head assembly and the bladder for controlling the flow of fluid from the bladder to the aperture.

2. The oral cleaning device of claim 1, further comprising a nozzle positioned in the aperture in the neck and head assembly to jet the water out of the device.

3. The oral cleaning device of claim 1, wherein the neck and head assembly is removable and interchangeable with a second neck and head assembly having a different configuration to provide the user with a different cleaning implement.

4. The oral cleaning device of claim 3, wherein the second neck and head assembly is configured with a nozzle to simulate flossing, a brush with a nozzle for cleaning teeth, a brush with a nozzle for cleaning a tongue, or a tongue scraper with apertures.

5. An oral cleaning device having a body, and a head having an aperture, the oral cleaning device further comprising:
    a latex bladder positioned within the body and in fluid communication with a controlled release to release fluid within the bladder to the aperture, the bladder is further in fluid communication with a controlled opening to allow the flow of fluid from an outside source into the bladder, the bladder is expandable to allow a fluid to fill therein through the controlled opening and is resilient to exert a pressure on the fluid contained therein such that the fluid expels out of the bladder and out of the aperture when released by said controlled release; and
    where the head includes a nozzle positioned in the aperture of the head and sized for cleaning a portion of a user's mouth, and the head includes bristles positioned about the nozzle, the head further having a predetermined shape defined for a tongue brush, or a tooth brush.

6. The oral cleaning device of claim 5 wherein the controlled opening is a one-way valve assembly attached to one end of the bladder and positioned in a bottom portion of the body, the one-way valve assembly includes an opening that allows the one-way entrance of a fluid from an outside source into the bladder.

7. The oral cleaning device of claim 6, wherein the head is removably connected to the oral cleaning device.

8. The oral cleaning device of claim 7, wherein the head is interchangeable with a second head that includes a projecting edge that defines a plurality of openings in the projecting edge.

9. The oral cleaning device of claim 6, wherein the controlled release is defined by a valve control mechanism attached between the bladder and the head, the valve control mechanism includes a button that when pressed opens a valve to allow fluid in the bladder to travel to the aperture and when the button is released said valve closes to prevent the fluid in the bladder from flowing to the aperture.

10. An oral cleaning device comprising:
    a bladder to hold a liquid, the bladder is expandable and resilient such that the bladder tends to return to an unfilled position, the bladder being secured within a body which a user may grasp;
    a bottom portion having a one-way valve assembly secured to a first end of the bladder and the one-way valve assembly having an aperture sized to fit a faucet nozzle, such that when positioned over a faucet nozzle and the faucet is turned on, water will enter the bladder via the one-way valve assembly;
    a neck and head assembly attached to the body, the neck and head assembly includes an aperture in fluid communication with a second end of the bladder and is configured with a nozzle in fluid communication with a channel for jetting water out of the device and for cleaning a portion of a user's mouth, and wherein the neck and head assembly is defined to clean a first portion of the user's mouth and is interchangeable with a second neck and head assembly defined to clean a second portion of the user's mouth; and
    a fluid control mechanism attached between the second end of the bladder and the neck and head assembly, the control mechanism includes a valve that prevents water contained in the bladder from entering the channel and includes a release button that when pressed opens the valve to permit water contained in the bladder to enter the channel,
    whereby when the bladder contains water, the bladder having a tendency to return to unfilled positioned exerts a pressure on the water, such that the water is expelled out of the bladder and out through the nozzle in the neck and head assembly when the release button is pressed.

11. The oral cleaning device of claim 10, wherein the second neck and head assembly includes bristles positioned about the nozzle.

12. The oral cleaning device of claim 10, wherein the second neck and head assembly includes a projected edge with at least one opening to permit the liquid to expel from the head.

* * * * *